United States Patent [19]
Margery et al.

[11] Patent Number: 6,055,487
[45] Date of Patent: Apr. 25, 2000

[54] INTERACTIVE REMOTE SAMPLE ANALYSIS SYSTEM

[76] Inventors: Keith S. Margery, 775 Eglinton La.; Robin A. Felder, 1841 Fendall Ave., both of Charlottesville, Va. 22903; James C. Boyd, 2121 Whippoorwill Rd., Charlottesville, Va. 22901; J. William Holman, Rte. 1, Box 451, Earlysville, Va. 22936; John Savory, Rte. 2, Box 577, Keswick, Va. 22947

[21] Appl. No.: 08/859,240

[22] Filed: May 20, 1997

Related U.S. Application Data

[63] Continuation-in-part of application No. 08/343,773, Nov. 22, 1994, Pat. No. 5,631,844, which is a continuation-in-part of application No. 07/739,204, Jul. 30, 1991, Pat. No. 5,366,896.

[51] Int. Cl.$^7$ .......................... G01N 33/00; G01N 35/00
[52] U.S. Cl. ................... 702/84; 702/22; 702/85; 436/43
[58] Field of Search ................... 702/22, 66, 84, 702/85, 186; 436/43, 501; 700/9

[56] References Cited

U.S. PATENT DOCUMENTS

| | | | |
|---|---|---|---|
| 4,670,219 | 6/1987 | Nelson et al. | 422/63 |
| 4,676,951 | 6/1987 | Armes et al. | 422/65 |
| 4,781,891 | 11/1988 | Galle et al. | 422/64 |
| 5,366,896 | 11/1994 | Margery et al. | 436/48 |
| 5,532,941 | 7/1996 | Lin | 702/84 |
| 5,631,844 | 5/1997 | Margery et al. | 702/22 |

*Primary Examiner*—Kamini Shah
*Attorney, Agent, or Firm*—Sheldon H. Parker

[57] ABSTRACT

An bi-directional, interactive multi-station medical specimen analysis system for simultaneously analyzing a medical specimen at remote locations and accessing, for evaluation, the results of each of the analyses at a central laboratory is disclosed. The system is networked to a server for storing databases. A central laboratory, interacts with remote computers, through the server to review, evaluate and accept or reject specimen analyses. The server communicates with the plurality of dedicated computers, laboratory computer and a centralized computer through a LAN or WAN. Analytical instruments which are not equipped to communicate with a computer are connected through computer interface software which interprets the instrument language into the computer program language and the computer program language into the instrument language. The bi-directional, interactive system requests analytical tests, transmit the test results to the server databases and receives and displays data from the server databases. Laboratory based bi-directional, interactive software acquires and either displays test results from the server databases, reviews and accepts or rejects the test results and transmits the acceptance or rejection to the server databases.

5 Claims, 12 Drawing Sheets

INTERACTIVE REMOTE SAMPLE ANALYSIS SYSTEM

CROSS REFERENCE TO RELATED APPLICATIONS

This application is a continuation-in-part of U.S. Ser. No. 08/343,773, filed Nov. 22, 1994, issued May 20, 1997 as U.S. Pat. No. 5,631,844, which is a continuation-in-part of U.S. Application Ser. No. 07/739,204, filed Jul. 30, 1991, issued Nov. 22, 1994 as U.S. Pat. No. 5,366,896.

BACKGROUND OF THE INVENTION

1. Field of the Invention

The invention relates to an integrated analytical system which includes a remote analyzing instrument and a central monitoring station.

2. Description of the Prior Art

Dramatic improvements in industrial productivity and quality have been achieved with the application of computer related technology. Against this backdrop hospitals and hospital laboratories across the country have integrated computers into the hospital care system. Health care traditionally has been a difficult marketplace for automation because of the complexity of the procedures and the potential risks to human life if an error were to occur.

In confronting increasing pressure to reduce the cost of providing analytical results, many laboratories have centralized their services to conserve resources. By consolidating services, expensive equipment has less idle time and labor is used more cost effectively. However, centralization may adversely affect the sample-to-result turnaround time by increasing the distance of the centralized laboratory from the origin of the specimen. Frequently, analytical results must be obtained in a short time to provide information for rapid assessment of a situation so that corrective actions may be taken. In medical care, for example, the clinical state of a critically ill patient must be assessed and corrected before a life threatening condition occurs. Similarly, in the outpatient clinic, providing results of blood analysis to physicians while patients are still in the physicians' office is highly desirable because it obviates the need for a return appointment to discuss abnormal laboratory results. In industrial process control, real-time monitoring of the progress of chemical reactions by on-site analytical techniques prevents dangerous conditions or loss of products.

Up to now, improvements in the turnaround of results have been obtained either by dedicated rapid specimen transportation systems or by simplifications of analytical techniques that make the specimen analysis faster. Pneumatic tube systems, mobile carts, and human messengers have been used with some success to transport specimens rapidly to the central laboratory. However, these systems are expensive to install and maintain; and in some facilities retrofitting of pneumatic tube systems or cart systems is not possible.

Additionally, there has been much interest in simplifying analytical instruments so that non-technical employees can perform complex analysis. For example, physician's office laboratories have been equipped with a new generation of analyzers that can provide rapid results with minimal operator training. Unfortunately, the results provided by many of these simple analyzers are not as precise or accurate as the results obtained in the centralized laboratories. Furthermore, the adequacy of quality control has frequently been overlooked. New pending federal regulations require that only trained medical technologists perform laboratory tests. These regulations will prohibit the physician or paramedical personnel (e.g. nurse or respiratory therapist) from performing clinical laboratory tests.

A user interface indicates a software design that makes many of the complex codes for computerized instrument control and data input/output transparent to the user. Simple English language commands should be used to give instructions to a computer, analytical instrument and/or robot. Although many companies have developed simple-to-use computer, instrument and robotic-control languages accessible to most computer programmers, unfortunately the programming associated with communication with other devices remains incomplete.

Nationally, there has been an increasing trend toward performance of selected laboratory tests using whole blood analyzers located close to the critical care patient's bedside. This approach has the advantage of providing an average test turnaround time of 5 minutes. Up to now, this testing generally has been performed by individuals with minimal training in medical technology. Newly instituted Joint Commission of the American Hospitals Organization and College of American Pathologists ancillary testing regulations require a similar level of quality control as that required by larger laboratories offering similar services. Because most personnel working in intensive care settings have neither the experience nor desire to perform rigorous quality control, this function will be assumed by trained medical technologists from the clinical laboratory in many centers. Staffing these satellite whole blood analysis laboratories with medical technologists will result in much higher costs unless an automated alternative can be developed.

Remote technology could also find a use in laboratories peripheral to the medical center. The estimated 100,000 physicians office laboratories in the United States perform approximately 25% of total laboratory testing. Besides being profitable for physicians, the major incentive for performing laboratory tests in the physicians office is the rapid turnaround. Rapid analysis results in prompt initiation of treatment, reduction in patient stress, and a reduction in repeat office visits. The major criticism of physician office testing is the lack of adequate quality control. Proposed regulations recently issued by the Health Care Finance Administration (HCFA) to carry out the Clinical Laboratory Improvement Act of 1988 (CLIA) require each physicians' office laboratory to monitor and document quality assurance, proficiency testing, safety, and instrument maintenance. Employees must meet the qualifications set forth by the Department of Health and Human Services and be involved in a continuing education program. Robotics can provide many physicians with the laboratory services they require on site yet put the responsibility of monitoring quality, hiring and training qualified personnel, and maintaining instruments in the hands of a local commercial laboratory or hospital. Connection of the remote laboratory in the physicians office to the commercial laboratory could be through a telephone line.

Additional uses can be in the field of microbiology, as many microbiology tests have been reduced to simple devices which can be easily handled by robot. The remote laboratory can be configured to also include microbiology analysis.

The next major medical frontier is the use of molecular biology for identification and diagnosis of genetic-based diseases. Once the aberrant gene is identified, gene therapy eventually may allow replacement of defective genes.

Molecular biology is already providing many new tests which are being used to identify various genetic diseases (e.g., cystic fibrosis and sickle cell anemia). There has been a rapid expansion in the number and variety and simplicity of analysis based on genetic markers. The remote laboratory can be used for rapid, on site testing based on molecular biology.

Hematology analysis are usually performed on heparinized whole blood specimens. The heparin (usually in the specimen tube before the blood is drawn into it) serves as an anticoagulant so that the blood remains free flowing. Hematologists are usually concerned with analysis such as white blood cell concentration, the number of subpopulations of white cells, red cell concentration and morphology gradients, and platelet concentrations.

U.S. Pat. No. 4,670,219, Nelson et al, discloses an analysis system having a first region in which sample materials are stored at an appropriate storage temperature and an analysis region which is maintained at a controlled and stabilized temperature higher than the temperature of the first region. The transfer mechanism includes a liquid handling probe that is mounted on a probe transport carriage, and a drive for moving the transport carriage between the first and second regions. The transport carriage includes a storage chamber connected to the liquid handling probe, thermal energy supplying means in heat exchange relation with the storage chamber, and thermal sensor means carried by the transport carriage. Means responsive to the thermal sensor supplies thermal energy to the transport carriage to maintain the storage chamber at substantially the same temperature as the analysis region.

U.S. Pat. No. 4,676,951, Armes et al, discloses an automatic system for analyzing specimens which have been selectively treated. The specimens are arranged in a plurality of specimen trays with each tray containing a plurality of specimens. A work station selectively moves the trays one at a time from the tower to selectively deliver reagent or analyze the specimen in the tray. A control system is adapted to sequentially actuate the work station to properly sequence the system so that the reagents are administered to the respective specimens and the specimens have been analyzed after a desired incubating period.

U.S. Pat. No. 4,781,891, Galle et al, discloses an automatic analyzing apparatus for effecting chemical analysis for various sample liquids such as blood, urine and the like, comprising a sample delivery pump for metering a sample liquid into a reaction cuvette, a reagent delivery pump for delivering to the reaction cuvette a given amount of a given reagent selected from a plurality of reagents contained in a reagent cassette, to form a test liquid, a feed mechanism for successively supplying reaction cuvettes along a circular reaction line, a plurality of photometering sections arranged along the reaction line for effecting a plurality of measurements for each test liquid at different time instances to product a plurality of results.

A major difficulty facing implementors of remote analytical stations in health care is the lack of electronic communications, software, or hardware standards in clinical instruments. Many clinical laboratory analyzers, for example, operate as discreet devices with only a RS-232C port for the output of analytical data. Remote, computerized operation of instruments requires an electronic communication standard that allows many of the instrument electronic functions be accessible to the host computer. For example, an analyzer which has been internally programmed to self-calibrate on a predetermined schedule should not initiate a calibration cycle at the same time as an irreplaceable medical specimen is being injected into the sampling port.

Point of care testing is an important component of caring for the critically ill patient. Rapid assessment of oxygen delivery, acid bases status, electrolytes and glucose are essential. Options for providing these services are rapid delivery of specimens to a central facility using a pneumatic tube system, staffing a satellite laboratory, or having on-site instrumentation. The first two approaches are extremely expensive. The third is a viable option but requires the application of new technologies such as "hand-held" analyzers. The expense of these devices is considerable being in the range of $10 per specimen analysis.

The laboratory disclosed herein is an alternative model to the large centralized laboratory facility. One of the major disadvantages of centralized laboratory facilities is the extended length of time to obtain analytical results. Long turnaround time can result in compromised patient care, particularly in intensive care units. A high cost specimen transportation system has been the traditional method to reduce specimen transit time.

The problems outlined above have been overcome through the instant invention which serves as an alternative to the centralized laboratory by providing analytical services near to where the specimen is obtained without substantially increasing the need for additional labor. The instant invention consists of a method to control commercially available analytical instruments via a computer interface linked to novel computer software. The analytical, electronic and mechanical performance of the laboratory is monitored remotely through electronic, radio or optical link. The automated remote laboratory provides extremely rapid turnaround, eliminates the cost of labor for specimen processing, reduces the risk from contaminated specimens, reduces staff training and results in improved patient care.

SUMMARY OF THE INVENTION

An interactive multi-station medical specimen analysis system for simultaneously analyzing a medical specimen at remote locations and accessing for evaluation the results of each of the analyses at a central laboratory is disclosed. The system comprises a server for storing databases, including patient demographics and analysis results and for permitting automatic retrieval and storage of data on an interactive basis by a plurality of computers. A plurality of analytical instruments at remote locations each interacting with a dedicated computer, having a display, to activate and interact with the analytical instrument. The computer serves as an interface between the analytical instrument and the server. A central laboratory, having display means, computer to interacts with the dedicated computers through the server to review, evaluate and accept or reject specimen analyses. Communication means connect the server with the plurality of dedicated computers, laboratory computer and a centralized computer. An analytical instrument to dedicated computer interface interpret the instrument language into the computer program language and the computer program language into the instrument language. Dedicated computer interactive means request analytical tests, transmit the test results to the server databases and receive and display data from the server databases. Laboratory computer interactive means for acquire and display test results from the server databases, review and accept or reject the test results and transmit the acceptance or rejection to the server databases.

The server database can temporarily store files which consist of information requested from, or being transmitted to the computer.

BRIEF DESCRIPTION OF THE DRAWINGS

The objects and features of the invention will become more apparent from the following drawings when read in conjunction with the specification.

DESCRIPTION OF THE PREFERRED EMBODIMENTS

Figure 1:
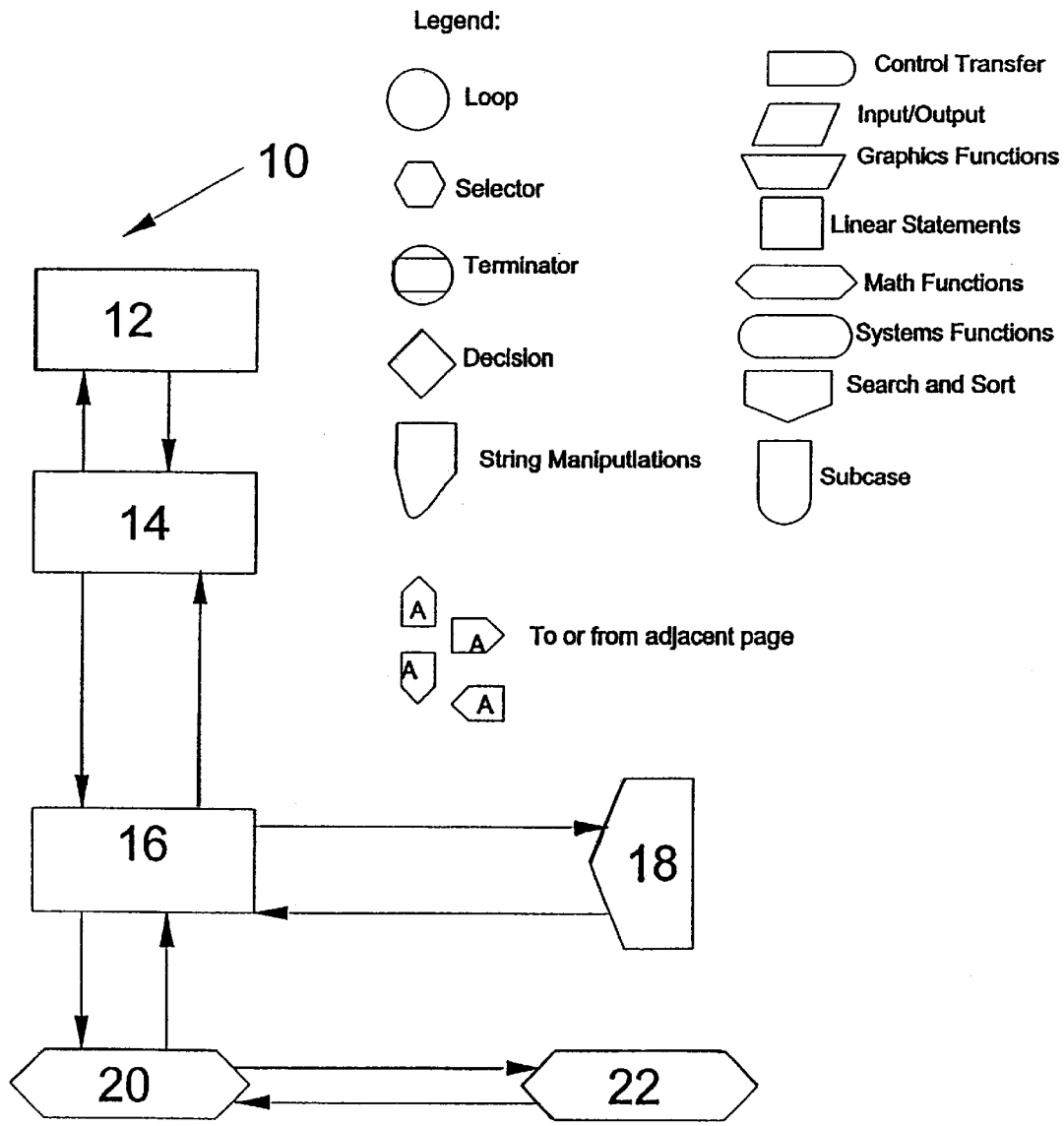
FIG. 1 is a flow diagram of the disclosed, interactive system.
Figure 2:
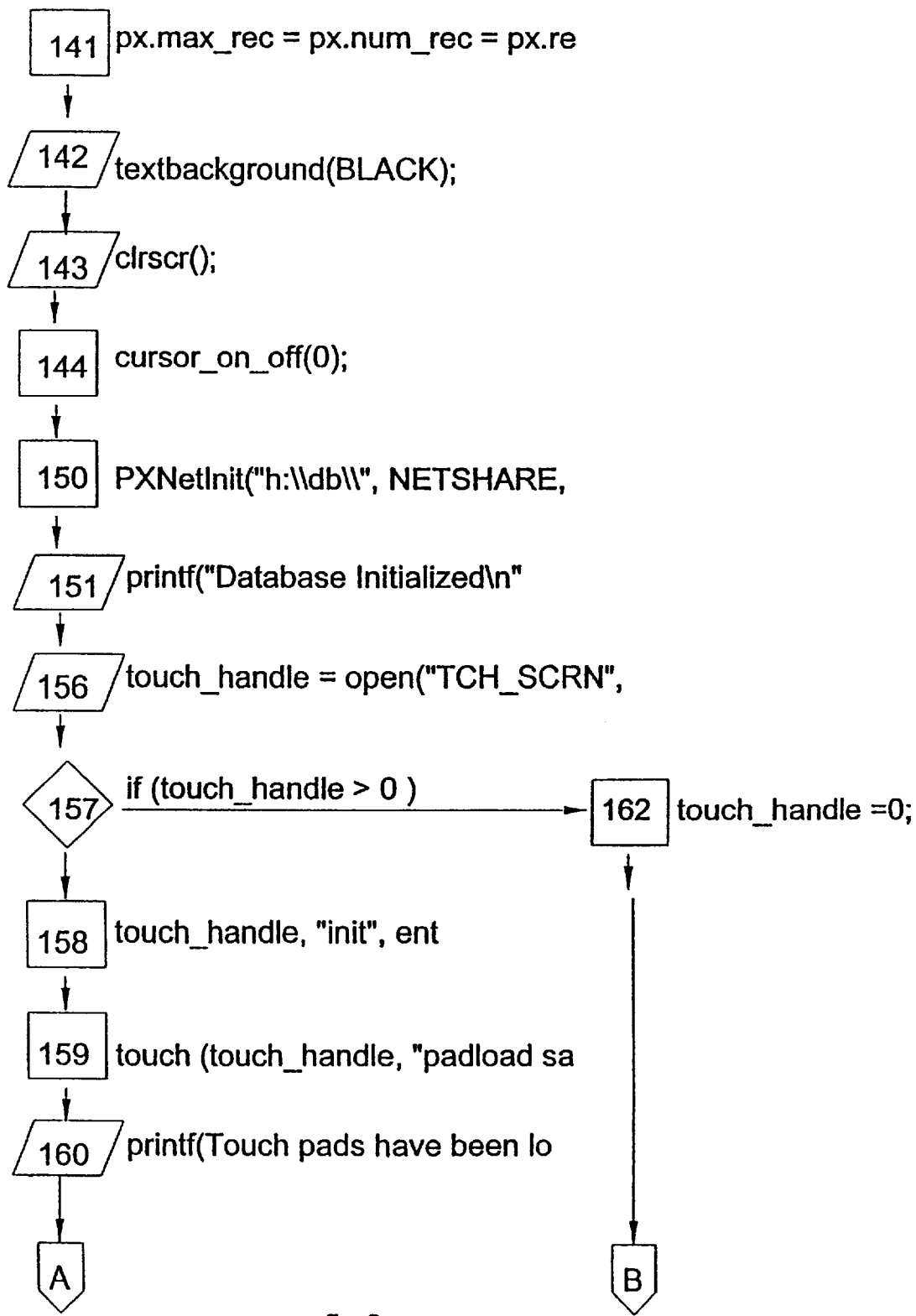
FIGS. 2 through 5 are flow diagrams of the laboratory unit.
Figure 3:
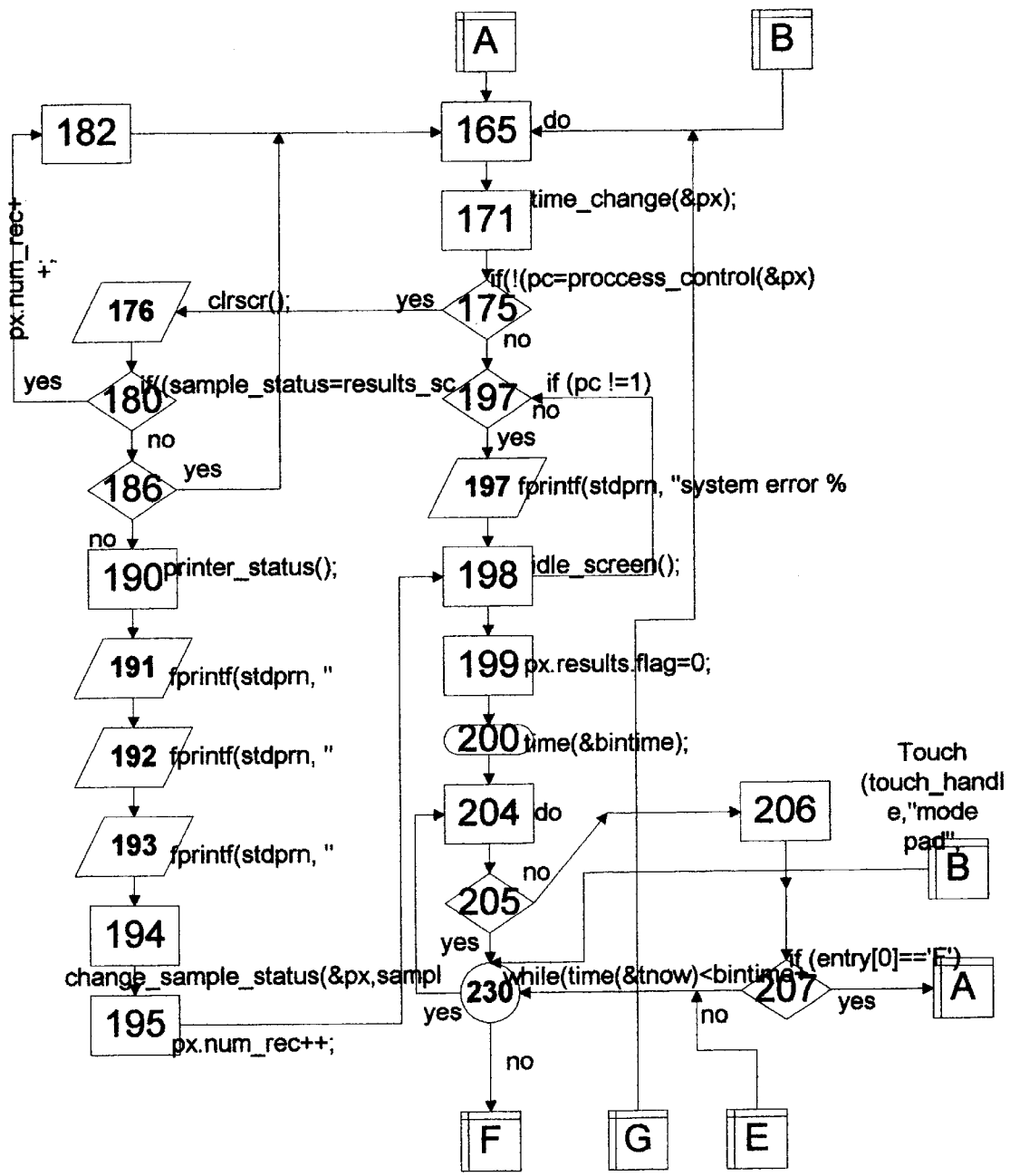
Figure 4:
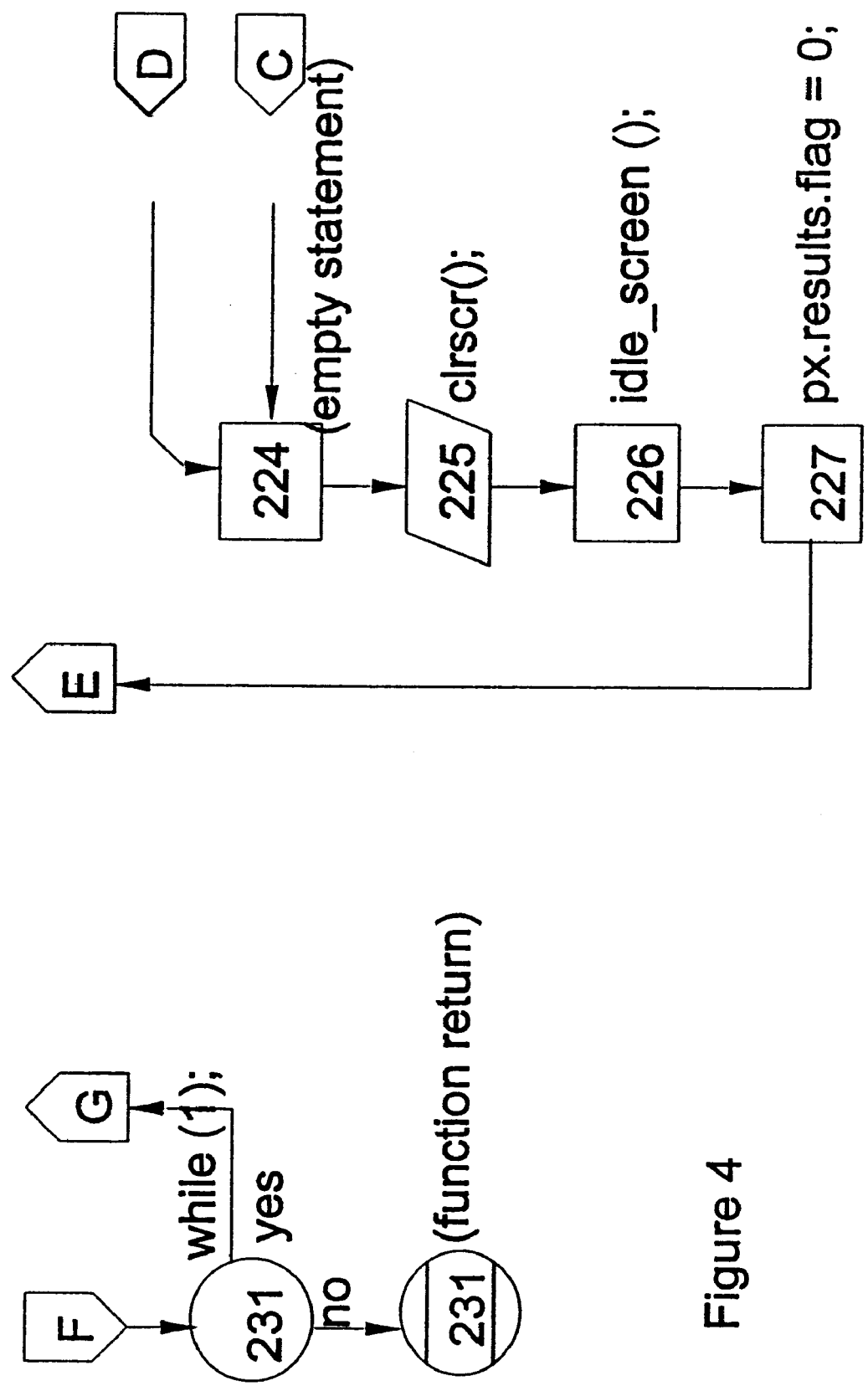
Figure 5:
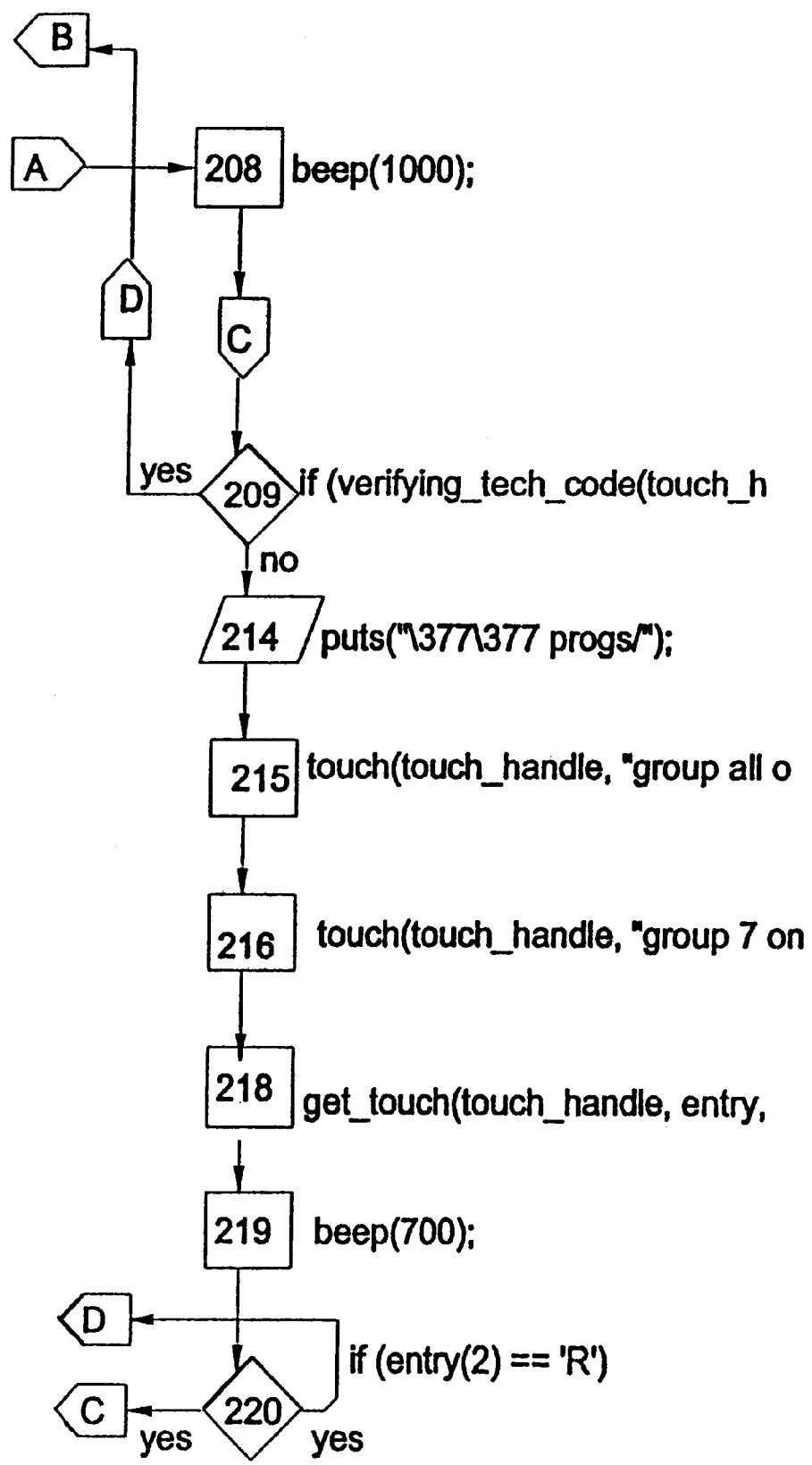
Figure 6:
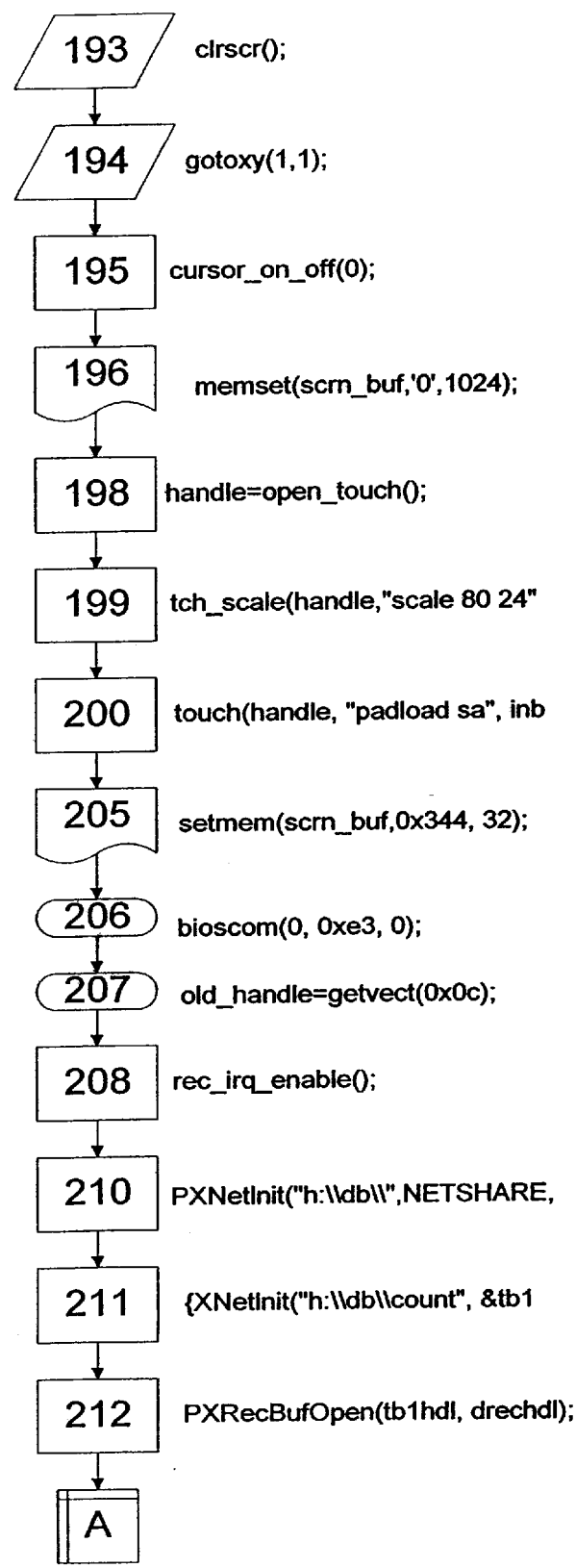
FIGS. 6 through 12 are flow diagrams of the analysis station.
Figure 7:
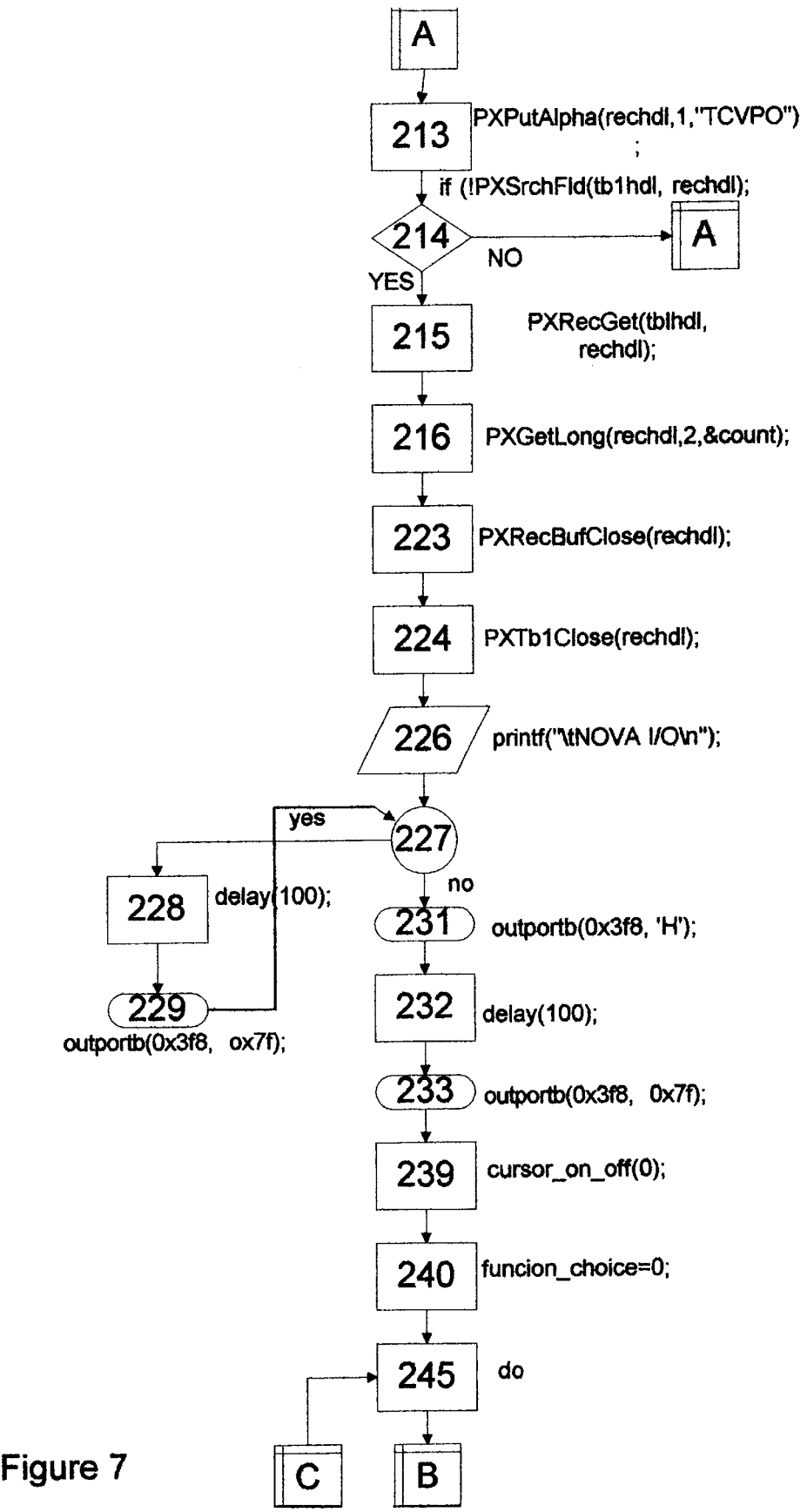
Figure 8:
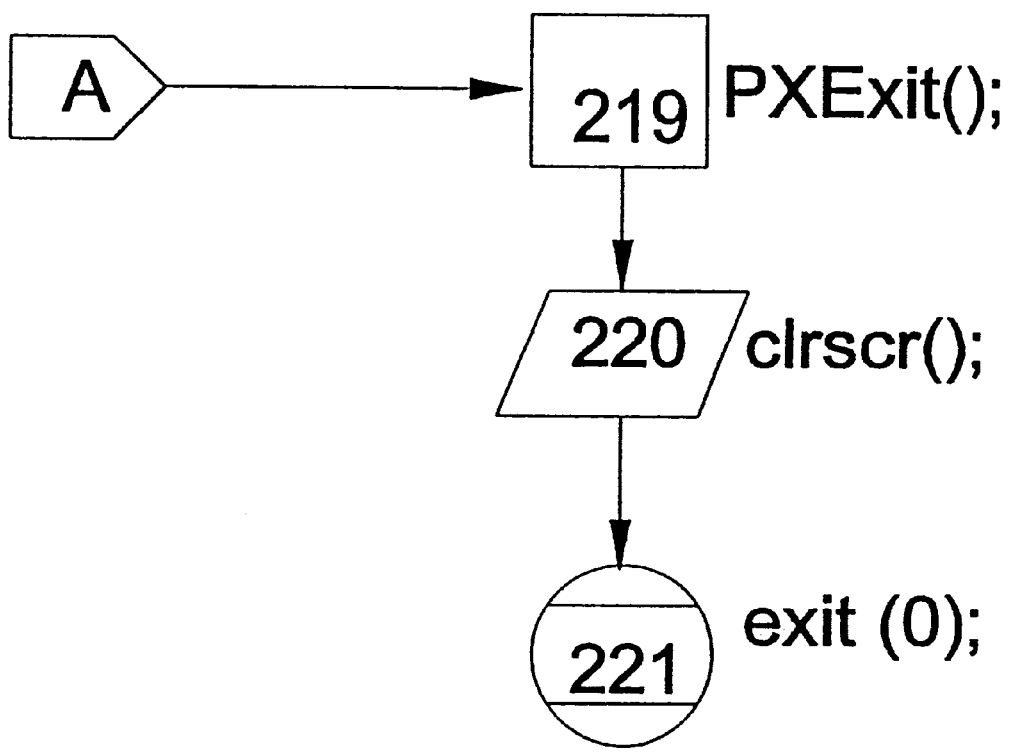
Figure 9:
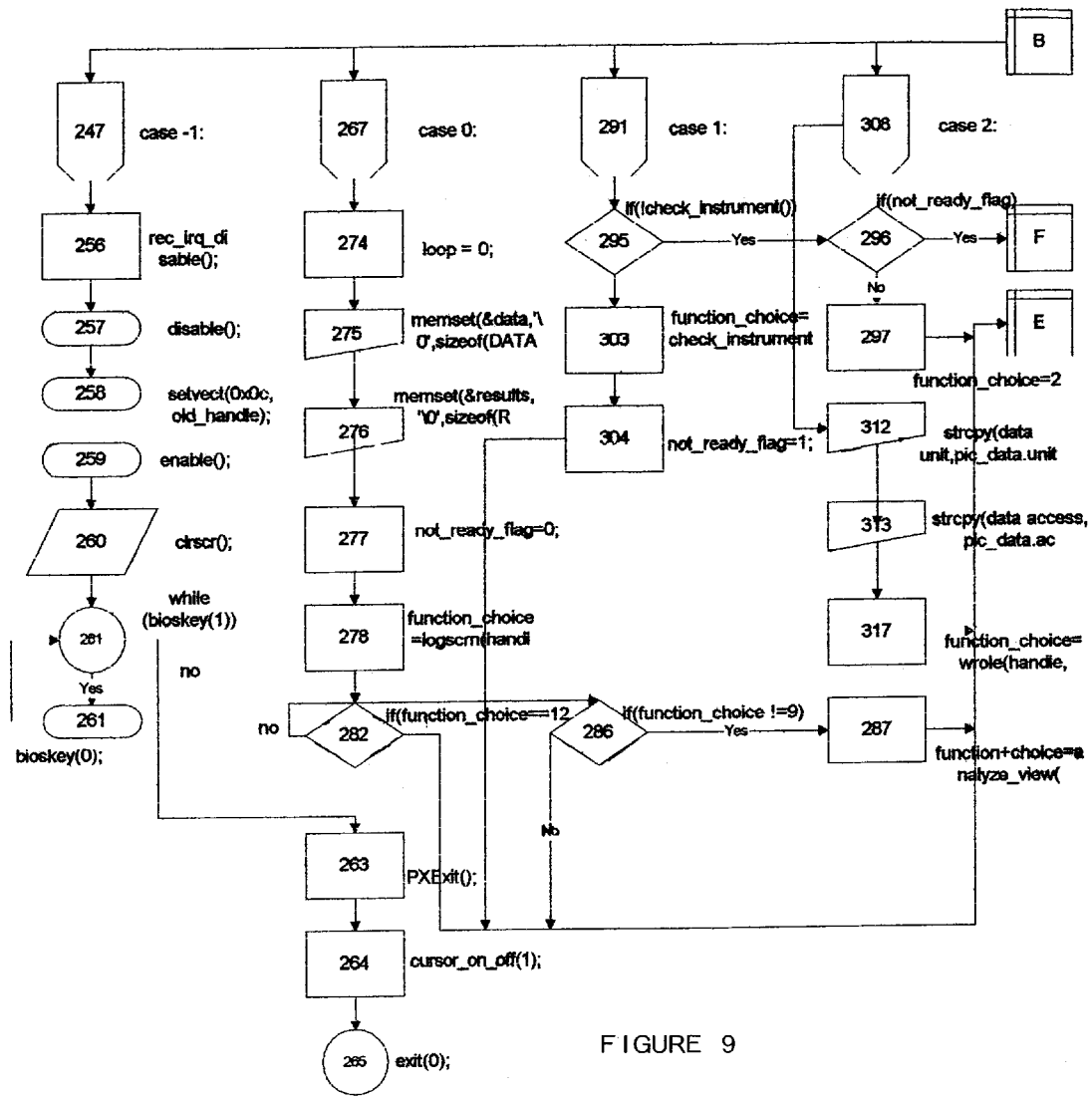
Figure 10:
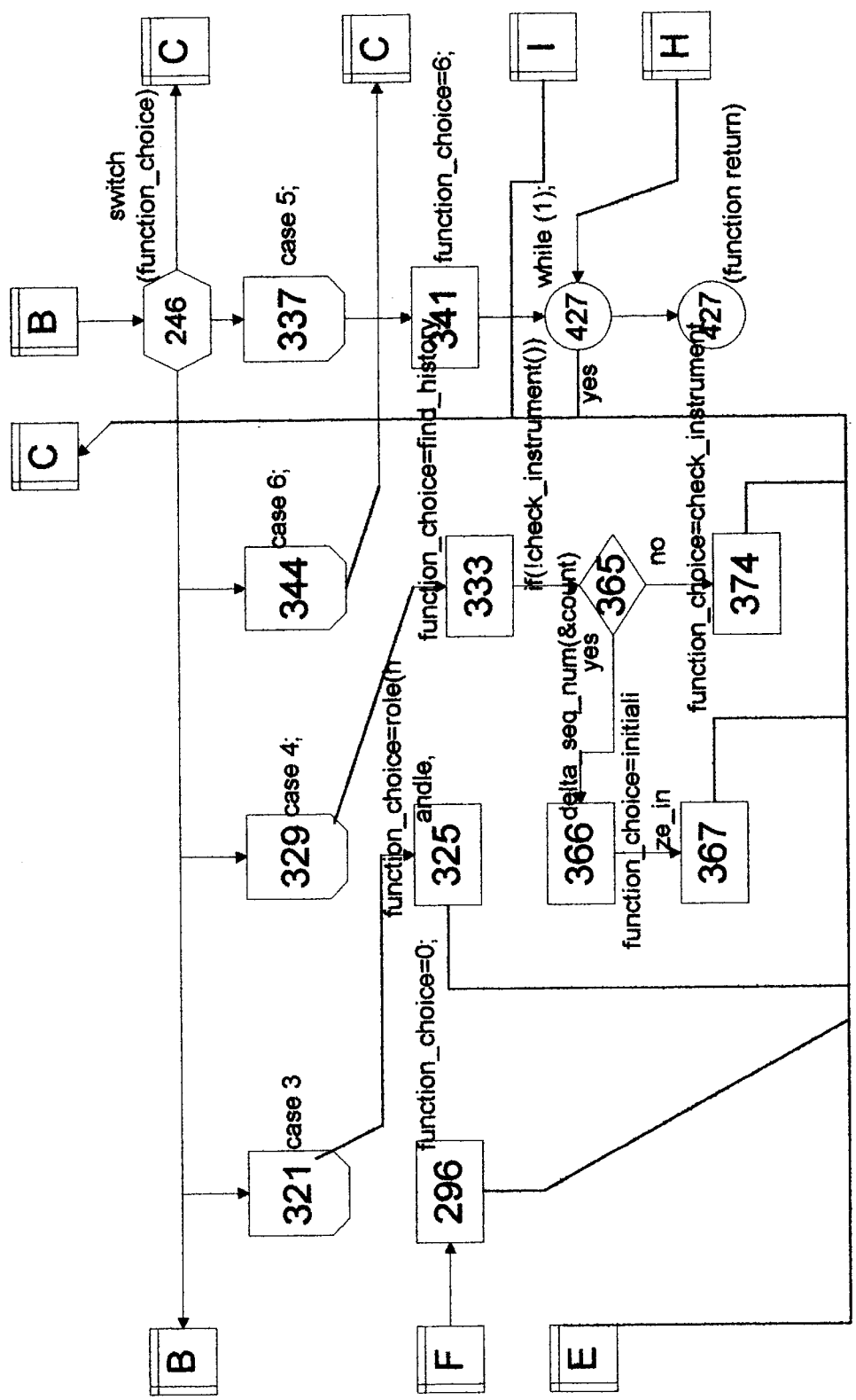
Figure 11:
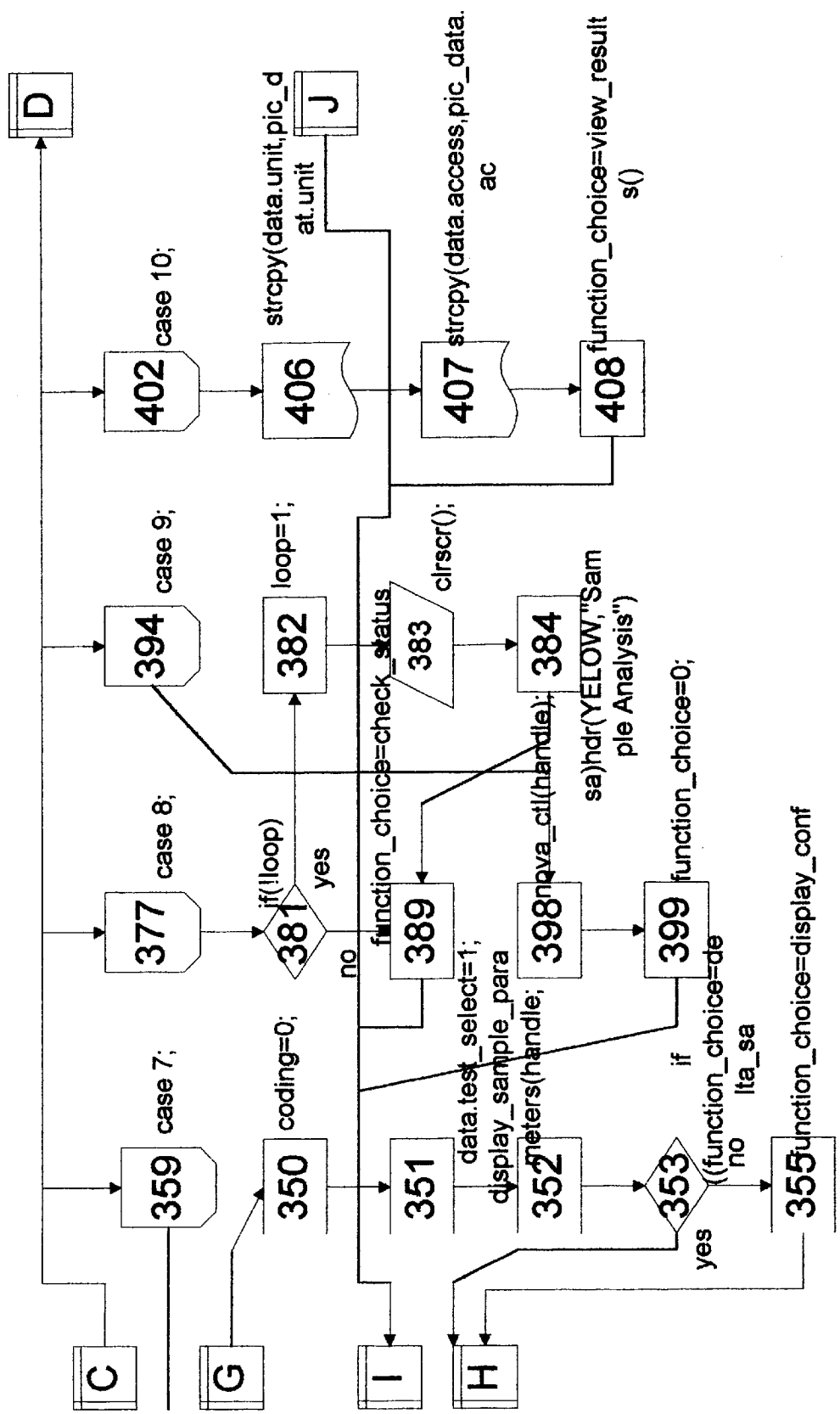
Figure 12:
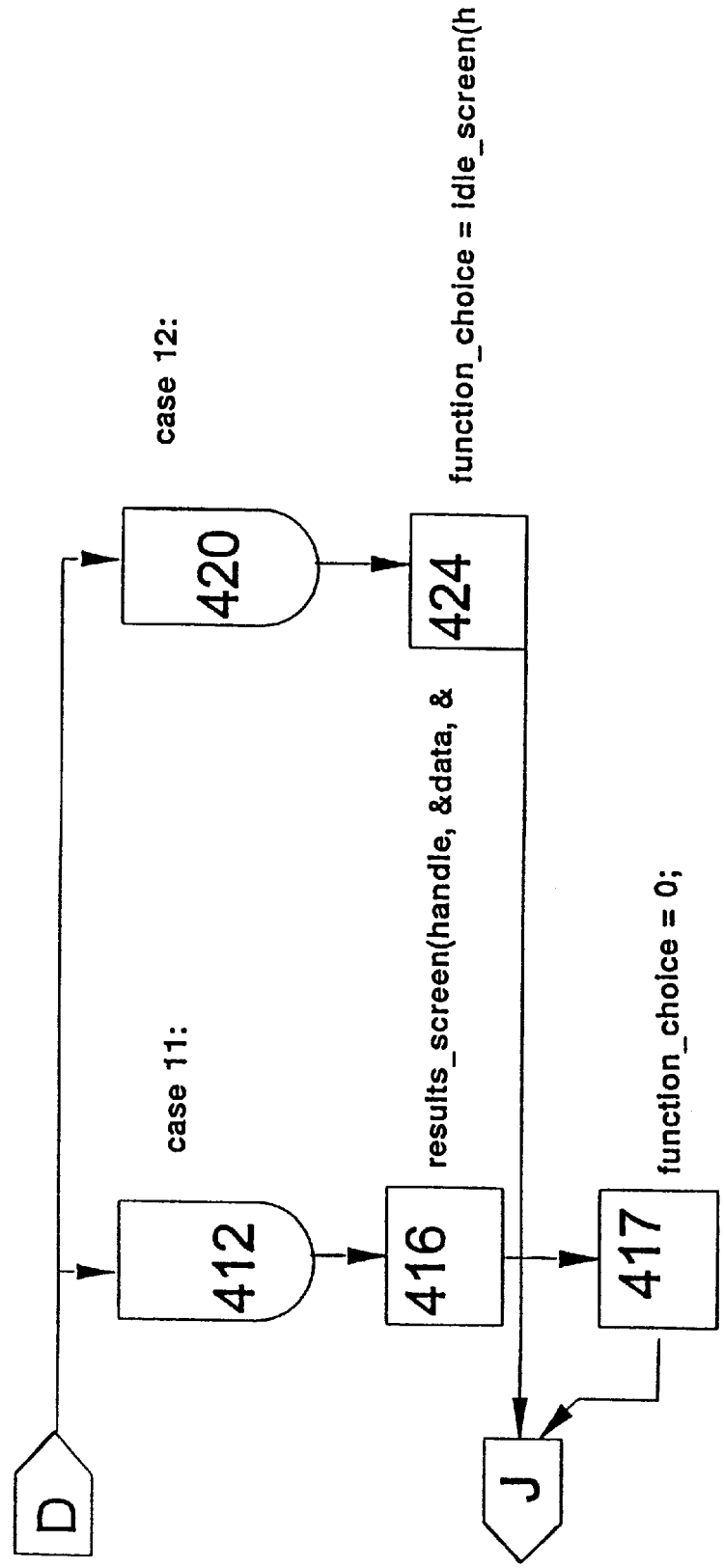

Although many laboratories have centralized critical care services to conserve resources, centralization has often been at the expense of providing optimal patient care. The instant disclosure combines the convenience of bi-direction satellite Analysis Stations located in, or close to, a critical care unit with the optimal analysis benefits of a centralized laboratory. The Analysis Stations can, for example, provide whole blood analysis of blood gases ($pCO_2$, $pO_2$), pH, electrolytes ($Na^+$, $K^+$, $Cl^-$), glucose, and hemoglobin by utilizing conventional clinical laboratory instruments linked to the centralized Laboratory Unit via computer. The remote analysis of blood samples is being used in the description herein, however it should be noted that other fluids can also be tested, such as urine. A medical technologist in the Laboratory Unit has the ability not only to view the analysis results, but also the ability to control many functions of the Analysis Station. The individuals utilizing the Analysis Station need not be laboratorians as their sole responsibility is to introduce the specimen to the system in much the same way as it would be given to a messenger or placed in a pneumatic tube system for delivery to a central laboratory. Viewing stations, which only allow monitoring of the test results and status and other operating parameters, provide the ability for administration to directly run administrative reports.

The bi-directional, interactive system has two distinct embodiments, with variations, which will be apparent to one skilled in the art, within each embodiment. In one embodiment, Analysis Stations consist of an analytical instrument and computer. These Stand Alone Analysis Stations are easy to use and relatively economical, the pricing being largely dependent upon the analysis instrument incorporated in the Station. The Stand Alone Analysis Station requires manual introduction of the specimen into the analyzer. In an alternate embodiment an automated system embodiment uses a robot arm to present the blood specimen to the analytical instrument. The original Automated Analysis Station is disclosed in full in copending U.S. application Ser. No. 07/739,204 and is incorporated herein as though cited in full. The automated system disclosed herein is an embodiment thereof and therefore only an overview of the sequence of steps is set forth herein. Both the Stand Alone and Automated Analysis Stations are linked to the main Laboratory Unit via a computer network.

Monitors, including touch screen, are incorporated into the system both at the Analysis Station and the Laboratory Unit.

In order to clearly set forth the scope of invention, the following component definitions are provided.

Laboratory Unit

The Laboratory Unit consists of an individual computer, preferably equipped with a color monitor, and small hard drive for storing the screen images and the corresponding program. The individual computer is advantageous for small hospitals or labs, however in most instances the Laboratory Unit will be networked to the main computer system with both the screen images and program accessed directly therefrom. The commands are given to the program through any input system, such as touch screen or keyboard. The color monitor is beneficial to provide visual distinction between read-outs, emphasize problems, etc. For example, arterial specimens provide red numbers, and venous specimens blue numbers and flashing numbers indicate that results are out of the reference range. The last 10 analysis obtained on the patient can be displayed in tabular form to facilitate interpretation of out-of-range results or to establish trends. It is preferable to add an alarm system, activated by the satellite central computer, which is activated if a pending result is not verified within 10 seconds. The alarm would require user interaction to eliminate, thereby ensuring rapid turn around time. The software program allows the medical technologist to view results and carry out the appropriate action. Patient results are sent from the Laboratory Unit to the network file server where they are stored in a results database.

Server

A dedicated micro-processor can be utilized for running all required programs to operate the system, however in the preferred embodiment a multitasking operating system and shared processors are used. The acquisition of patient demographic information from the main hospital information system and return of completed laboratory test results to the main system is also run through the server. A Laboratory Information System interface serves to translate the patient information received from and sent to the hospital main computer system to the server. Interfacing with the main computer system allows for current patient demographics to be accessed to be used in conjunction with the instant system. The interface utilized can be a standard computer to computer interface meeting the American Society for Testing and Materials (ASTM) specifications, such as set forth in Designations: E 1381-91 and E 1394-91 which are incorporated herein by reference. Once approved, the results received from the analysis are sent to and stored in the hospital's main computer system, thereby further updating the patient's demographics.

Local Area Network (LAN) and/or Wide Area Network (WAN)

Physical computer to computer communication is achieved through any standard commercially available hardware and software. An example of hard-wired networking is the ANSI/IEEE 802.3 (CSMA/CD) standard, utilized as the LAN communication protocol with Novell version 3.1, or other appropriate networking software and interface cards. In large installations where several individual hospitals are linked to a central facility, the LANs can subsequently be connected to either a user third party WAN. Optical fibers, twisted pair, or coax cable are used to couple the network computers together. Computer to computer communication can also be achieved through satellite, telephone lines, TV cable networks, Internet or any other protocols allows for bi-directional communications.

Monitoring Station

One or more monitoring stations can be provided within the system, dependent upon size and proximity. The monitoring stations are not connected to analysis equipment and do not have input capabilities to alter or run analysis programs. The monitoring stations do, however, provide the administration, or head personnel, the capability to view and/or run reports on the test results, number of tests run, system parameters, test status, etc. This avoids the Analysis Stations being use for monitoring purposes.

Analysis Station

Each Analysis Station consists of a computer equipped with a video monitor, preferably color, and input means. In instances where the analyzer is provided with networking capability directly to a main computer, the local computer can be eliminated. As stated heretofore, the input means can be a mouse, touch sensitive screen, keyboard or other input means used in the art. The computer must be equipped with two ports which are compatible with the analyzer and monitor. It is advantageous in many applications to provide a printer to provide hard copies of the screen results. Software has been written to display choices of patient demographics, analytical tests to be performed, and modifications to the outputted data (e.g. patient temperature and hemoglobin which influence the calculation of the results of the analysis) which may be selected by the user of the laboratory.

In the Stand Alone Analysis Station a user inserts the sample into the analytical instrument, allowing the instrument to aspirate the required amount of specimen.

In the Remote Analysis Station, the user places a sample on a receiving area, thereby activating the robotic arm to commence processing of the sample. The robot arm allows rapid entry of multiple specimens as well as totally unattended operation.

The arm used is a commercial laboratory robot (CRS, Plus, Toronto, Canada). Additional components of the robot include the robot controller and host microcomputer. In addition the robot comes equipped with gripper sensors which give feedback indication of the forces applied by the robot fingers. Gripper sensors provide simple touch sensing which can detect the presence or absence of an object in the robot end effectors.

The robot is programmed to perform simple "pick and place" operations on 3 mL plastic syringes containing the fluid for analysis, and also is trained to use several peripheral tools designed for complex procedures such as cap removal and replacement, specimen mixing, and air bubble removal (burper). The robot arm must be capable of a high degree of repetitive movement precision (repeatability of 0.05 mm). To maintain such precision an orientation device is incorporated into the design of the robot environment to allow the robot to recalibrate its location should it become disoriented.

One advantage to the Remote Analysis Station is the ability to include multiple analytical instruments within the reach of the robot. This allows for a wide variety of tests to be run on multiple analyzers with only one sample and a one time effort by the user. Further benefit is achieved from use of the robot when handling contaminate specimens or working in a hostile environment. The remote, robotically operated system allows for analysis of toxic materials without human intervention. The robotic arm can easily be programmed to remove the container cap, fill the container, insert the material into the testing apparatus, replace the cap and store the container.

The interactive system allows the user to select a specific analysis to be run from the analysis available on the particular instrument. Although only the specific analysis are displayed, the entire profile capable by the analysis instrument is actually measured on each sample. The running of the entire profile is advantageous in several ways. The interface is simpler to write, as the selected tests do not have to be sorted from the unselected tests. Although the unselected tests could be eliminated at the server, the accessibility of all tests capable of being run is an advantage. For example, in the event only a blood gas is initially requested, however subsequently it is decided that results on the remaining available tests are required, these test will be available. Other parameters such as $FIO_2$ and patient temperature can be adjusted and default values of no NFG ($FIO_2$ given, and 37°) are incorporated for the convenience of the user.

The programs that run on the Analysis Station computer are adaptable to any commercially available database system, such as SQL or Microsoft ACCESS. Alternatively the databases can be custom written utilizing a compiler such as Turbo C. which takes the "C" source code and compiles it into an executable program.

The Analysis Stations can be located in a variety of locations within the same hospital which house the Laboratory Unit at various doctors offices, clinics or hospitals or a combination thereof. Although the analysis stations are generally used to input the specimen, all or part of the information contained within the system is accessible based on user's clearance. This allows for any user with the appropriate clearance level to access data contained within the system from any station.

Analyzer to Computer Interface

There are three basic areas in which instrument standardization is necessary: sample preparation and introduction, operator input of information to the analyzer, and output of information from the analyzer to the user. In order to standardize these areas interfaces are incorporated. An universal interface was disclosed in U.S. Ser. No. 07/739,204, which has been incorporated herein, wherein a system simplified communication between a microcomputer and clinical instrument by establishing a standardized bi-directional communications protocol. Both the universal interface and the dedicated interface operate on the same basic principle—translation of instrument codes to interactive program codes and vise versa.

Current clinical analysis instruments are being designed with interactive analysis capabilities and require little or no modification. Up until recently, however, clinical analysis instruments, even if computer compatible, were not designed for interactive analysis. Hence, the need for standardization of data communications and analyzer interface hardware. The interface translates input commands to codes or actions recognizable by the analyzer. Features not normally available to the user, such as electrode real-time response and full instrument status, are also reported by the interface, thereby establishing a remote monitor and control mechanism for the interfaced instrument. The availability of the interface allows the disclosed system to be compatible with the older analysis hardware, as well as the current equipment having interactive capabilities.

The operating system controls the interface, which in turn commands and monitors the clinical analyzer. The server controls the information flow to the interface and provides (a) requests to the interface for instrument operation and status and (b) commands to the interface to initiate the desired instrument operation. This arrangement maintains complete instrument functionality as designed by the manufacturer while allowing remote monitoring and operation of the instrument.

When necessary, the interface minimizes modifications of the commercial analytical instrument. The analytical instrument control signals are translated, through use of a look-up table, into a standardized format on an erasable/programmable read only memory (EPROM) chip contained on an interface card. This format is compatible with signals used in the remote Analysis Stations. This translation allows rapid interfacing of a variety of analytical instruments which potentially could be incorporated into the laboratory unit. Furthermore, the interface card facilitates packaging of the instrument output into a format that simplifies communication software at the host computer. The interface permits remote control of all calibration cycles, chamber evacuation, washes and sampling mode, retrieval of patient and calibration results, initiation of instrument settings for the patient's temperature and hemoglobin concentration, barometric pressure, time, and date.

Standard electronic hardware is used in the design of both the universal and dedicated interfaces, such as Intel Corporation (Santa Clara, Calif.) integrated circuits. A microprocessor, peripheral interface adapter, universal synchronous/asynchronous receiver/transmitter, erasable programmable read-only memory, static random-access memory, and support circuitry compose the current standard interface microcomputer.

A unique set of software commands, within the universal interface, is used for each clinical instrument to allow the instrument to be controlled by the interface. The instrument-specific software translates instrument data into a standardized string for transmission to a host computer. Alternatively, specific software can be written for each analytical instrument used as a "dedicated" interface. Although not as convenient as a universal interface, dedicated interfaces can be used to overcome specific hardware problems encountered in less compatible instruments.

In an example universal analytical instrument interface, a standardized output string for each instrument is made up of an instrument identifier, a mode of operation, the instrument command, device real-time status, results, error checking, and a transmission terminator. The instrument identifier field holds a lead character and a two-digit number (e.g., Corning: COI). The mode of operation can be a single ASCII character, ie. A-Automatic, C-Command, D-Diagnostic, E-Error, R-Results. The default mode is Command. If the interface detects an instrument operational error, the Error mode is indicated. The Diagnostic mode can be set by the host computer to enable routines on board the interface to assist in instrument evaluation and trouble shooting. The Automatic mode, also externally selectable, assists in the quality-control operation of the instrument. Both of the interfaces are capable of automatically testing calibration results and operations and, if an error is detected, a selected number of attempts to correct the malfunction are initiated.

The Command-field is a character selected from a standard command set developed for this interface. Use of a standard Command set for all target analyzers simplifies the interface/operating system instrument control routines. The Command set is divided into subsets that perform calibrations, retrieve data, set operation parameters, ascertain device status, and control manual instrument function. One set of commands for any instrument or group of instruments reduces the demands on the host computer for specific device evaluation. Instrument real-time status is an 11-character set and decoded to indicate full instrument operational status. Most target instrument functions can be indicated within this field.

Instrument results are within delimiting brackets to allow ease of extracting results. Any sequence of instrument results could be mimicked by other similar devices used with the interface. For example, if two different blood gas analyzers are controlled by an interface, both will report results in the same sequence, irrespective of the original manufacturer's design (pH, $pCO_2$, $pO_2$, etc.). This sequencing allows the host computer to be unaffected by changes resulting from manufacturer design or user instrument selection, which simplifies instrument control and processing of results.

As an example of a dedicated interface, modifications to the Corning 178 blood gas analyzer were limited to removal of a switch logic board (board no. 7) and replacement with a connector card and custom cable. Commands that the blood gas analyzer used to initiate operation were loaded to a particular personality card memory location and an interrupt was triggered. Data as well as instrument operation were indicated from the memory output and, with proper decoding, a real-time status was returned. Use of the real-time scan gives the Laboratory Unit full monitoring of the blood gas analyzer and, in conjunction with the input Commands, complete control and remote monitoring of the analyzer. An added benefit offered by the real-time scan was monitoring of electrode response of the analyzer at any time. The addition of this scan, provided the ability to trouble shoot instrument errors from a remote site.

Analytical Instrument

Any commercially available computer compatible analytical instrument can be placed in the Analysis Station because of the unique design of the interfaces, hardware, and software. The analytical instrument must, however, have the ability to be automated and capable of being interfaced, either with a universal or dedicated interface, with a computerized system. These instruments also include hand held point of care instruments. The system of interfacing is not necessarily limited to hardwiring. Bi-directional infrared, radio frequency and other non-hardwired communications are also applicable. The data is transferred via non-hardwired means to the computer where it is then transmitted to the lab for processing as set forth herein.

Instruments which were not manufactured to be interactive with computerized systems can readily be altered to interface these instruments with the instant system. Instruments which cannot be incorporated with the instant systems are those which require human input on a step by step basis. Instruments which do not have the capability to be totally automated, can be utilized with the system on a limited basis. It should be noted herein that although analytical instruments, such as a blood gas analyzer is being described herein, any medical instrument which can be made compatible with a computerized system can be controlled and monitored through the instant system.

The system, as disclosed herein, is referring to laboratory-to-remote instrument interaction. This interaction can be between the Laboratory Unit and multiple Stand Alone and/or Automated Analysis Station instruments. However as each interaction takes the same route, for simplicity the interaction between the Laboratory Unit and a single Analysis Station will be described herein.

Many instruments used in the clinical laboratory are designed to be autonomous, easy-to-operate devices. Provisions are made for sample introduction, user data input through a keypad or other peripheral device, and reporting instrument status and test data. Instrument operation is controlled by the user or by an internal computer that coordinates instrument operation. Each manufacturer of laboratory instrumentation follows its own protocol for device control commands and instrument communications. Often data from the analyzer is limited solely to final calibration set point reports and results for patients' samples. Most instruments will report derived data to an external device, such as a printer or host computer, according to established communications protocols (RS-232C, Electronic Industry Association Recommended Standard 232, version C).

Operational control and monitoring of an analyzer must not only include access to the data produced by the instrument but also allow for total peripheral control of the analyzer.

Process Sequence

Server

The server is a storage and manipulation device used in the standard network manner as well known in the prior art. The uniqueness lies in the database software which enables the hardware to interact with the Analysis Stations and Laboratory Unit.

Laboratory Unit

1. The system hardware is checked for existence of monitoring equipment.
2. The database file access is established.
3. If 1 or 2 above do not meet the predetermined standards, the system is aborted. Errors can be displayed on the screen and a reset opportunity presented after error correction.
4. The Laboratory Unit program periodically checks the server to determine if unprocessed analysis results have been received from the analytical instrument. The time period between checks with the server can be set by the Medical Technician Operator and can vary based on time of day. If no results are present for the Operator's review, the save screen is initiated. If results are present for viewing, the program proceeds to the next Command.
5. Once an unprocessed test result is recognized in the Laboratory Unit, the result is retrieved by the Laboratory Unit.
6. Upon receipt of the unprocessed test result, a display is brought up onto the monitor showing the units where the sample originated. Simultaneously, an alarm is activated at periodic time intervals to alert the Operator. An audio alarm is generally utilized, however any type of appropriate alarm or combination can be used.
7. The alarm is deactivated upon Operator's input and the commencement of program activation.
8. Once acknowledged the test results are displayed on the screen displaying the test results in the programmed format. The amount of data on the screen can vary based on hospital policy, Operator's preference, etc. This can include a request for past test results or other patient information which has been incorporated within the program for access.
9. Operator's ID codes are requested to verify that the Operator reading the results is known to the system. If incorrect ID is entered, the system goes back to step 6.
10. The screen remains active until an indication of acceptance or rejection is received.
11. Upon acceptance of the test results, the Laboratory Unit program returns the accepted results to the appropriate database within the server. Once returned to the server, the test results are available to the Analysis Station on request basis. As an alternative, an indicator can be provided at the Analysis Station monitor to indicate the completion of the analysis review. Alternatively, a hard copy print out can be automatically provided once the test results are obtained by the server.
12. The accepted test results are transmitted to the hospital main computer database for storage.
13. Rejected test results are returned to the server and saved until manual or global deletion.
14. The system is them reset, returning to step (4).

Analysis Station

The Analysis Station preferably has accessible three modes, Analysis, Review and Maintenance.

Analysis Mode

1. Check system hardware for existence of monitor equipment.
2. Establish database file access (open database engines), and read "COUNT" database for Patient sample number.
3. Establish serial connection with analyzer
4. Initialize analyzer to standby mode
5. If any of steps (1)–(4) fail, the system will abort the remaining sequence and display the error reading on the screen.
6. Upon activation by user, ID is requested and can be, if desired, a double entry verification system.
7. The system waits for the user to enter the appropriate Login ID sequence. If interaction time is exceeded, the system returns to save screen. Although not critical, it is preferable to have a "save screen function" incorporated in the system to protect the monitor.
8. The user access and verify codes are tested for correctness. If either the access or verify code is incorrect, the system remains on the login screen to allow unlimited attempts to access the system. The system will go to the save screen at a predetermined time if there is no user interaction.
9. Screen displays Mode Selection based upon the user's ID codes. If the codes indicate an engineer or medical technologist is operating the system a Maintenance Mode will appear (Step 39). ID codes representing a user (nurse, aide, etc.) will display the analyze/review screen. An entry of Analysis proceeds to Step 10; and entry of Review proceeds to Step 29.
10. The system checks the analyzer to confirm that the instrument is ready for analysis. If it is not ready, an alarm is activated to advise the user that the system is not available. The screen goes to the login screen of Step 7.
11. The Analyze sample screen is displayed, enabling relevant commands (scroll up, down, enter, search by ID number, esc).
12. The screen displays a list of valid units from the "UNITS" database, defaulting to last selected unit by given user. The default unit follows the different access codes.
13. The system waits for the user to select the desired unit. In the event the user selects the ID option, the system goes to Step 26. If there is no interaction with the system the login screen is reactivated and the system returns to Step 7.
14. Once the unit is selected the user searches the patient roster database, "PATIENTS", for patients in the given unit.
15. The system displays the "Select Patient" screen, selected unit name and enables relevant commands (scroll up, down, enter, search by ID Number, esc).
16. The screen displays a list of valid patients for the selected unit.
17. The system waits for the user to select the desired patient. If the dead time is exceeded the system returns to the login screen at Step 7.
18. The system displays the patient demographics screen with relevant commands enabled (Patient temp, Fio2, Coding, test profile, enter, clear, esc).
19. The system displays the selected patient, ID number and location. Displays default values for temp (37.0° C.), fio2 (%), coding, test profile.
20. The system waits for the user to select the desired patient demographics. If interaction time is exceeded, the system returns to the login screen at Step 7.
21. Upon user pressing "Enter", the analyzer is prepared for analysis, the user is prompted to place valid sample in the docking port.

22. Once the analyzer probe is fully extended, a command to proceed with sample aspiration is sent. Upon sample retrieval, the system alerts the user to remove sample from the port. A patient sample number (an internal number generated by the software to provide a unique patient ID) is incremented and stored in the "COUNT" database.
23. Normal instrument function continues until the sample analysis is complete. Once operation is complete, the instrument is queried, by the system, for results and errors.
24. The results, patient demographics, and instrument errors are stored in the results database "RAW".
25. The instrument continues its normal analysis cycle of washing out. Displays "Instrument Washout". At the completion of the washout cycle, the system goes to the login screen at Step 7.
26. If the search by patient ID option is chosen in Step 13, the system displays the Search by ID screen and enables relevant commands (numeric pad, clear, enter).
27. The system prompts the user to enter desired ID. If no response from the user is entered within the specified time the system returns to the login screen at Step 7.
28. User enters the Patient ID and the system searches patient database "PATIENTS" for matching ID number. If the ID is present the system goes to Step 14. If the ID is not located the screen shows "Invalid ID" and allows re-entry of ID number.

Review Mode

29. The system displays the "review results" screen and enables relevant commands (scroll up, down, enter, search by ID number, esc).
30. A list of valid units in "UNITS" database is displayed, defaulting to the last selected unit by given user. The default unit follows the different access codes.
31. The system waits for the user to select desired unit. If the user selects to search by ID, the system goes to Step 42. If inactivation time is exceeded the screen returns to the login screen of Step 7.
32. The selected unit is used to search the patient roster database for patients in the given unit.
33. The system displays the "Select Patient" screen, selected unit name and enables relevant commands (scroll up, down, enter, search by ID Number, esc).
34. The system displays a list of valid patients for the selected unit.
35. The system waits for the user to select the desired patient. If interaction time is exceeded, the system returns to login screen at Step 7.
36. The patient results screen is displayed with relevant commands (print results, display previous 10 results, esc).
37. Patient results and demographics are displayed giving analysis results, pending or failed.
38. The system waits for user input. The user can chose to "clear" or "print and clear". If interaction time is exceeded, it returns to login screen at Step 7.

Maintenance Mode

39. The system displays instrument maintenance screen with relevant commands (all switches available on analyzer, esc.).
40. Wait for Operator input. If interaction time is exceeded the screen goes to login screen at Step 7.

Automated Analysis Station

The automated analysis station is disclosed in its entirety in the copending parent application. To maintain a continuity and to demonstrate the compatibility of the automated and stand alone systems, the following automated analytical sequence is set forth briefly as follows:

41. Steps 1 through 20 are same as Stand Alone Analysis Station.
42. The system requests the robot computer to open the receiving area door.
43. The system requests the user to place the sample in a single sample receptacle. If the sample is not received within the receptacle within the predetermined time, the system returns to Step 7.
44. Verification of the analysis and placement of the sample is requested by the system. If interaction time is exceeded, the system returns to login screen at Step 7.
45. Upon verification, the system closes the door and instructs the robot to begin the analytical sequence.
46. The robot lowers its actuators (fingers), grasps the syringe and moves it to a mixing chilling chamber.
47. Following a 30 second mixing chilling cycle, the syringe is removed from the mixer by the robot which then places it in a pneumatically driven uncapping device.
48. The system determines if there is sufficient sample volume for an accurate blood analysis. If all system checks are acceptable then the robot closes its end effectors to grasp the syringe at the correct location for accurate insertion into the instrument. In the event all system checks are not acceptable, the screen displays an error message and activates an audible alarm.
49. The system rechecks the readiness of the analysis instrument. If the instrument does not indicate "ready" the system displays an error message and activates the alarm.
50. Upon issuance of the ready mode, the robot places the syringe into the sample port of the instrument.
51. The instrument aspirates the required volume of the specimen and initiates the analysis.
52. The instrument sends a completed signal to the system instructing removal of the specimen.
53. The system directs the robot to position the syringe in the burper which ejects the air bubble by advancing the syringe plunger and simultaneously washing the tip.
54. The system returns the syringe to the decapping/capping station for recapping.
55. Once recapped, the syringe is returned to the mixer chiller to maintain specimen integrity.
56. Repeat of Steps 24–28 of Stand Alone Analysis Station.
57. Upon receipt of an acceptance from the Laboratory Unit the robot is directed to remove the syringe from storage for appropriate disposal.
58. Upon review, if the sample is not acceptable a retest can be ordered at which time Steps 47–56 are repeated.

Use of the Automated Analysis Station allows for a retesting using the same sample to be done at the discretion of the reviewing medical technologist.

FIG. 1 is a flow diagram of the interactive system 10. The Analysis Station 12 is provided with a CPU 14 as described in more detail heretofore. The flow of the information from Analysis Station 12 to Laboratory Unit 18 is identical whether the Analysis Station 12 is a Remote or Stand Alone unit. The data received from the CPU 14 is transmitted to the server 16 where it is processed. The server 16 contacts the hospital information system 22, through the LIS interface 20, to obtain patient information. The server 16's request is through use of the patient identification to obtain patient statistics required for analysis of the test results. Upon receipt of the patient information and calculation of values, the information is transmitted, upon request, to the Laboratory Unit 18. At the Laboratory Unit 18 the information is reviewed and accepted or rejected as described above. The results are sent back to the server 16 where they are "sorted". The rejected tests are sent back to the Analysis Station 12 where the user is notified of the rejection. The accepted results are sent to the Analysis Station 12 and to the hospital information system 22 where they are stored in the patients database.

FIGS. 2–5 illustrate, in flow diagrams, the program for the Laboratory Unit as described in U.S. application Ser. No. 08/343,773.

The code for the automated robotic station has been disclosed in the aforenoted application.

Compared to providing services in a central laboratory facility, there are considerable cost benefits of unmanned satellite laboratories. The advantages of reduced labor costs for sample transportation and laboratory staff, and reduced sample turnaround time outweigh the increased costs of equipment required for many laboratories. Studies of the cost-saving of the University of Virginia unmanned satellite robotic laboratory showed that it saved $19,900 per year in messenger time, $22,750 per year in nursing time, and $3900 per year in supplies. If the cost for additional laboratory technologist time required for quality control and maintenance of the unit was subtracted from these savings, the net operational savings were $38,650 per year. Compared with equipment purchase costs of $85,750, the system will pay for itself over three years. Preliminary data indicate that the average test turnaround from time of physician request to reported results is 10 minutes when using the satellite robotic laboratory compared with 72 minutes when the sample is sent "stat" to the central laboratory.

One obvious alternative to an unmanned satellite laboratory is a satellite facility. The expense of such an approach is excessive requiring at least 4–5 full time equivalents for 24 hour per day/7 days per week operation. Without a very high workload, the manned satellite laboratory is not an economically sound approach to critical care testing.

The automated remote laboratory provides rapid turnaround of critical care tests, eliminates the labor costs associated with specimen processing, reduces the risks from contact with contaminated specimens, has less staff training than other on-site testing approaches, and provides improved patient care.

What is claimed is:

1. A bi-directional interactive multi-station specimen analysis system for simultaneously analyzing a specimen at remote locations and accessing for evaluation the results of each of the analyses at a central laboratory, said system comprising:

a server for storing databases, including patient demographics and analysis results and for permitting automatic retrieval and storage of data on an interactive basis by a plurality of computers, a plurality of analytical instruments each interacting with a dedicated computer to activate and interact with the analytical instrument and to serve as an interface between said analytical instrument and said server, said dedicated computer having display means;

a central laboratory computer to interact with the dedicated computer through the server to review, evaluate and accept or reject specimen analyses, said laboratory computer having display means;

communication means connecting said server with said plurality of dedicated computers, said laboratory computer and a centralized computer;

analytical instrument to dedicated computer interface to interpret the instrument language into the computer program language and the computer program language into the instrument language;

dedicated computer interactive means for requesting analytical tests, transmitting the test results to the server databases and receiving and displaying data from the server databases; and laboratory computer interactive means for acquiring and displaying test results from the server databases, reviewing and accepting or rejecting said test results and transmitting said acceptance or rejection to said server databases.

2. An bi-directional, interactive system as in claim 1 wherein said database temporarily stores files consisting of information requested from and being sent to said computer.

3. An bi-directional, interactive system as in claim 1 wherein:

said dedicated computer interactive means including a sequence to initialize the interaction between the user and the analysis instrument.

4. An bi-directional, interactive system as in claim 3 wherein said dedicated computer display means displays an initialization screen which once activated commences the sample analysis sequence.

5. An bi-directional, interactive system as in claim 1 further comprising a monitoring station, said monitoring station accessing said databases in a viewing mode without database input capabilities.

* * * * *

UNITED STATES PATENT AND TRADEMARK OFFICE
CERTIFICATE OF CORRECTION

PATENT NO. : 6,055,487 Page 1 of 1
DATED : April 25, 2000
INVENTOR(S) : Keith S. Margrey et al.

It is certified that error appears in the above-identified patent and that said Letters Patent is hereby corrected as shown below:

Column 1,
Line 12, the following paragraph is inserted:
-- U.S. Government Rights
This invention was made with United States Government support under Grant No. HL62211, awarded by the National Institutes of Health. The United States Government has certain rights in the invention. --

Signed and Sealed this

Twenty-ninth Day of June, 2004

JON W. DUDAS
*Acting Director of the United States Patent and Trademark Office*